United States Patent
Kocagoz

(10) Patent No.: US 6,265,182 B1
(45) Date of Patent: Jul. 24, 2001

(54) ANTIBACTERIAL SUSCEPTIBILITY TEST

(76) Inventor: Zuhtu T. Kocagoz, Koza Sokak, 88/6 Gazi Osman Pasa, Ankara (TR)

( * ) Notice: Subject to any disclaimer, the term of this patent is extended or adjusted under 35 U.S.C. 154(b) by 0 days.

(21) Appl. No.: 09/423,087

(22) PCT Filed: May 4, 1998

(86) PCT No.: PCT/TR98/00005

§ 371 Date: Feb. 7, 2000

§ 102(e) Date: Feb. 7, 2000

(87) PCT Pub. No.: WO98/50578

PCT Pub. Date: Nov. 12, 1998

(30) Foreign Application Priority Data

May 2, 1997 (TR) ................................................. 97/0344

(51) Int. Cl.⁷ ............................. C12Q 1/18; G01N 33/53
(52) U.S. Cl. ............................................. 435/32; 435/975
(58) Field of Search ........................................ 435/32, 975

(56) References Cited

U.S. PATENT DOCUMENTS 4,820,428 * 4/1989 McLennan et al. .................... 435/32

FOREIGN PATENT DOCUMENTS

94/16079 A1   7/1994 (WO).

OTHER PUBLICATIONS

Cruz, F.O., Database WPI on EPOQUE, week 9109, London:Derwent Publications, Ltd., AN 91–058363, Class D16, BR 8903571 A, abstract.

* cited by examiner

Primary Examiner—Louise N. Leary
(74) Attorney, Agent, or Firm—Nixon & Vanderhye

(57) ABSTRACT

This invention provides a test kit which determines the susceptibility of bacteria to antibiotics within a short period of time, typically four to six hours. The kit utilizes a medium containing a color indicator that shows bacterial growth in a short period of time. In the kit, the metabolic activity of bacteria at a certain concentration of an antibiotic is determined by the change of the color of the medium. In this way, the susceptibility of the bacteria to this antibiotic is determined quickly without requiring instrumentation.

4 Claims, 1 Drawing Sheet

ANTIBACTERIAL SUSCEPTIBILITY TEST

This invention related to a method and product that enable the determination of the susceptibility of bacteria to antibacterials in a short period of time. The subject matter of this invention may be applied to various fields of microbiology other than methods used for diagnosis of diseases.

PRIOR ART

In the prior art, disk diffusion and broth or agar dilution methods are the most commonly used methods to determine the susceptibility of bacteria to antibiotics. These methods require overnight incubation. In recent years, various methods to determine quickly the growth of bacteria at a certain amount of antibacterial, have been developed. These systems are usually computerized and require an instrument to detect bacterial growth. Examples are the following:

Turbidometric methods which determine the turbidity of the media that occurs due to bacterial growth.

Nephelometric methods that determine the growth of bacteria by detecting the change in the light scattering of a light beam directed to the medium.

Colorimetric methods that determine the change in color of the media due to bacterial growth that either produce different colored products by using the substrates provided in the media or by pH indicators that change color due to pH change.

Radiometric methods that measure the radioactive carbon dioxide produced from a radioactive carbon source in the medium that is used during bacterial growth.

Fluorometric methods that measure the light emitted from fluorescent substances produced during bacterial growth.

Methods that measure the change in impedance due to the change in electric current conductivity of the medium during bacterial growth.

For the application of these methods, at least one instrument to measure light, color, electric conductivity or radioactivity is required. However, the kit which is the subject matter of this invention does not require an instrument, and the results can be directly obtained by visual observation. However, it can be easily adapted to automation by a suitable optical reader.

BRIEF DESCRIPTION OF THE INVENTION

The aim of this invention is to provide a method that will decrease the time required to perform antibacterial susceptibility testing to 4 to 6 hours which usually takes 18 to 24 hours by classical testing systems.

Another aim of this invention is to enable performing antibacterial susceptibility testing easily without requiring preparatory work or material.

Yet another aim of this invention is to produce an antibacterial susceptibility test kit that does not require instrumentation that can be performed in a basic laboratory and that can be easily adapted to automation if desired.

BRIEF DESCRIPTION OF THE DRAWING

The invention will be described in detail with reference to FIG. 1.

Figure 1:
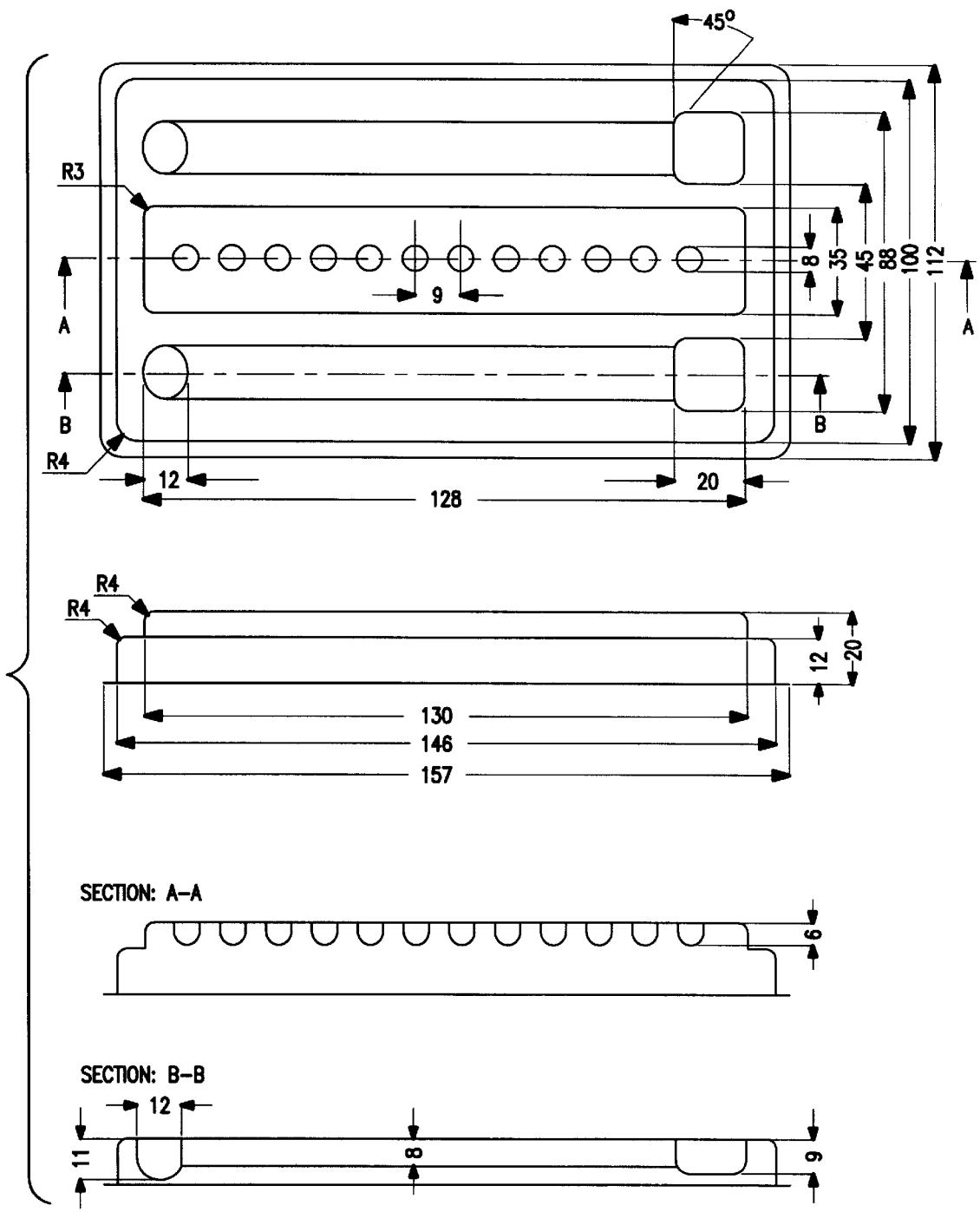
In FIG. 1, "A" shows the wells that contain various dried antibacterials and "B" shows the areas where diluent and media tubes are placed.

The tubes can be placed vertically into the 12 mm well that is shown at cross-section A—A. This enables the tubes to be kept upright during the application without requiring an additional support.

DETAILED DESCRIPTION OF THE INVENTION

This invention is related to a product that enables the determination of the susceptibility of bacteria to antibacterials in a short period of time. The most commonly used methods that do not use an instrument to determine antibacterial susceptibility require 18–24 hours since they are based on observation of a visible amount of turbidity created by multiplying bacteria. The above-described methods that give the result early require special instrumentation. With the kit which is subject matter of this invention, results can be evaluated visually without a need for an instrument.

The basis of the present method lies in performing the test using a special medium that contains a color indicator which is the key component of the kit. This medium enables the observation of the bacterial growth by changing its color due to the metabolic activity of bacteria without the need for extensive bacterial growth to create visible turbidity. The growth of bacteria at a certain concentration of antibacterial is determined by observing the change in the color of the growth medium, and thus the susceptibility of the bacteria to this antibacterial is determined. The formula of this growth medium is described below. This medium has the characteristic of supporting growth for the bacteria that are frequently tested for antibacterial susceptibility, including Gram (−) fermentative bacteria (enterobacteriaceae), Gram (−) non-fermentative bacteria (Pseudomonas, Acinetobacter species), some Gram (+) bacteria (staphylococci) and several other bacterial species. The content of the medium is adjusted so that the pH rapidly rises to alkaline during bacterial growth. As is known, Enterobacteriaceae produce acid by fermentation in the presence of sugars, in a microaerophylic environment and lower the pH of the medium. In some previously described methods, bacterial growth is identified using this feature. However, it is not possible to use this principle in bacteria like Pseudomonas that cannot effect fermentation. For that reason, the kit of the invention is formulated in a way to show the growth of all of the bacterial species listed above.

The feature that is unique to all of these bacteria is their ability to use the amino acids, the building blocks of proteins, as their energy source and carbohydrate based building blocks, when carbohydrates are not present in the medium. The first step to use amino acids to produce energy or conversion to carbohydrates essential for cell growth, is deamination. The amino group is released as ammonia into the medium. This is a very strong base and creates a rapid rise in the pH. If the medium contains substances that act like buffers, the pH change is restricted. Proteins are substances that have buffering characteristics. The amount of proteins in the kit is kept low for a rapid change of pH to alkaline but enough to support rapid bacterial growth. To accelerate the usage and deamination of proteins, carbohydrates are not included in the medium.

Bacterial growth and the pH change due to this is determined by the pH indicator phenol red, included in the medium. The pH is adjusted to 6.1 when the medium is prepared. At this pH, phenol red has a yellow color. When the pH rises to 7–7,5 phenol red turns to red. The plate contains dried antibacterials in the wells. Desired concentrations of antibacterials are obtained when an adjusted volume of inoculated medium is put into these wells. If the bacteria are susceptible to this concentration of antibacterial, it does not grow and does not create a change in the color of the medium; if it is resistant, than it changes the pH during growth and causes a change in the color of the medium.

The bacteria listed above require excessive oxygen when they are grown in a medium where proteins are the only source of energy and carbohydrates are not available for obtaining energy by fermentation in anaerobic conditions. Oxygen dissolves in the medium by penetrating from the surface, and for that reason, the amount of oxygen penetration is proportional to the surface area. The plates of the kit are designed in a way to keep a high surface/volume ratio.

The medium is prepared by mixing the substances and dissolving thoroughly. At this moment the color of the medium is red to orange (pH is around 6.9 to 7.0). The pH is lowered to 6.1 by adding approximately 5 ml of 0.1N HCl. At this moment the color of the medium turns to yellow (pH is measured to make sure that it is 6.1. If needed the pH is adjusted to 6.1 by adding either 0.1N HCl or 0.1N NaOH).

It is possible to produce and use the kit for two different purposes. In the first form, the test is prepared so that it determines the susceptibility of bacteria to various antibacterials, as it is in disk diffusion. The wells of the test plate are prepared so as to contain dried antibacterials at an amount to produce a final concentration of breakpoint value for susceptibility, that is internationally accepted (usually the value prepared by NCCLS—National Committee for the Control of Laboratory Standards if not otherwise required). In the second form, each row of wells contains decreasing amount of antibacterials since it is aimed to obtain Minimal Inhibitory Concentration (MIC) for each antibacterial.

The kit is comprised of a solution for suspending bacteria and a medium used for identification of the rapid growth of bacteria, a test plate, the wells of which contain dried antibacterials and a printed paper that describes the application of the method and evaluation of the results.

In use, 50 µl of medium is placed into the last well of the raw that does not contain any antibacterial as the medium control. A few colony of bacteria obtained from a fresh culture plate, are suspended in the solution to produce a turbidity of 5.0–1.0 McFarland. A measured amount (usually 100 to 600 µl) of this suspension is transferred into the tube and mixed thoroughly. Then, 50 µl of this bacteria containing medium is put into the wells that contain antibacterials and one well that does not, and incubated 4 to 6 hours at 35 to 37°C. The results are evaluated when color change occurs in the wells where medium stays yellow and resistant where it turns to red.

When determining MIC, the change in the color of the medium occurs in the wells that contain an antibacterial up to a certain concentration. The well that contains the lowest antibacterial concentration where there is no color change shows MITC.

What is claimed is:

1. A kit for performing a rapid antibacterial susceptibility test, comprising wells containing dried antibacterials and at least two places to hold a solution and test tubes, wherein said at least two places have sides designed so that the test tubes can be fitted tightly to hold said tubes vertically during the test.

2. A kit according to claim 1 wherein said solution comprises 100 mg peptone and 1000 ml distilled water.

3. A kit according to claim 2 wherein said solution is prepared by dissolving peptone in water and distributed to sterile tubes after being sterilized in an autoclave.

4. A kit according to claim 1 which further includes a medium comprising of 0.5–7.5 g peptone, 0.5–7.5 g meat extract, 0.5–10 g NaCl, 980 ml distilled water and 0.5–12 ml Phenol Red (sodium salt) 1% solution in water.

* * * * *